United States Patent [19]
Reid

[11] Patent Number: 5,140,857
[45] Date of Patent: Aug. 25, 1992

[54] FRIABILITY TESTING APPARATUS

[76] Inventor: Douglas J. Reid, Crabtree Cottage, Ballycar, Newmarket on Fergus, County, Clare, Ireland

[21] Appl. No.: 625,745

[22] Filed: Dec. 11, 1990

[30] Foreign Application Priority Data

Dec. 12, 1989 [BE] Belgium .................. 8901322

[51] Int. Cl.$^5$ .................................. G01N 19/00
[52] U.S. Cl. ............................ 73/573; 73/664; 73/7
[58] Field of Search ............... 73/571, 662, 663, 664, 73/7, 12, 573, 579, 668, 87, 577, 578

[56] References Cited

U.S. PATENT DOCUMENTS

| | | | |
|---|---|---|---|
| 2,844,777 | 7/1958 | Ross | 73/664 |
| 3,141,325 | 7/1964 | Hajian | 73/664 |
| 3,636,772 | 1/1972 | Bennett | 73/7 |
| 4,297,888 | 11/1981 | Hirai et al. | 73/664 |
| 4,733,151 | 3/1988 | Butts | 73/664 |

FOREIGN PATENT DOCUMENTS 0116859 10/1978 Japan ..................... 73/664

*Primary Examiner*—Hezron E. Williams
*Assistant Examiner*—Rose M. Finley
*Attorney, Agent, or Firm*—Scully, Scott, Murphy & Presser

[57] ABSTRACT

The invention provides a friability testing apparatus which has an electrically excitable vibrator (10, 12) for vibrating a capsule (14) containing material to be tested. The apparatus includes a microprocssor (20) which proivdes an output waveform with a frequency which is determined by an oscillator (22). The output of the microprocssor drives a power amplifier (18) which controls the vibrator. An accelerometer (16) supplies signal to the microprocessor, so that the operation of the vibrator is maintained within predetermined limits.

8 Claims, 2 Drawing Sheets

ABILITY TESTING APPARATUS

BACKGROUND OF THE INVENTION

This invention relates to a friability testing apparatus. In one application of the invention, the apparatus can be used to test the friability of diamond particles.

A device known as a "Friatester" is currently used to test the friability of diamond particles. This device includes a round cylindrical capsule which is closed at its ends and which accommodates a hard spherical ball. In use, diamond grit the friability of which is to be tested is introduced into the capsule. The capsule is reciprocated back and forth in the direction of its axis with the result that the ball is thrown from end to end inside the capsule. Particles of grit are impacted by the ball and sandwiched between the ball and the relevant end of the capsule at each stroke, with the result that they are crushed. After the device has been in operation in this way for a set number of cycles, the grit is subjected to screen testing and a friability index (F.I.) is computed from the mass of the unbroken particles as a percentage of the mass of the original particle charge. The F.I. computed in this way has become an industry standard and has value to purchasers of diamonds who wish to know how the diamonds will perform in industrial applications such as in saws or abrasives.

In the known "Friatester" the capsule containing the material whose friability is to be tested and the steel ball, is reciprocated by means of a motor-driven crankshaft and connecting rod arrangement. With this kind of drive it is not possible to control the vibrations accurately or to vary them to suit different materials or classes of materials. In addition, despite rigorous calibration, the mechanical nature of the "Friatester" renders it liable to mechanical faults, such as wear, which to repeatability of performance which is less than optimum.

SUMMARY OF THE INVENTION

Friability testing apparatus according to the present invention comprises electrically excitable vibrator means for vibrating a capsule in which material of which the friability is to be tested is placed in use, amplifier means for applying an exciting signal to the vibrator means, processing means for generating the exciting signal in accordance with one or more predetermined criteria and a sensor associated with the vibrator means which is arranged to provide a feedback signal to the processor means to maintain the operation of the vibrator means within predetermined limits. The predetermined criteria of the exciting signal may include one or more of the duration, frequency, amplitude and waveform of the signal.

BRIEF DESCRIPTION OF THE DRAWINGS

The invention will now be described in more detail, by way of example only, with reference to the accompanying drawings in which.

DESCRIPTION OF A PREFERRED EMBODIMENT

Figure 1:
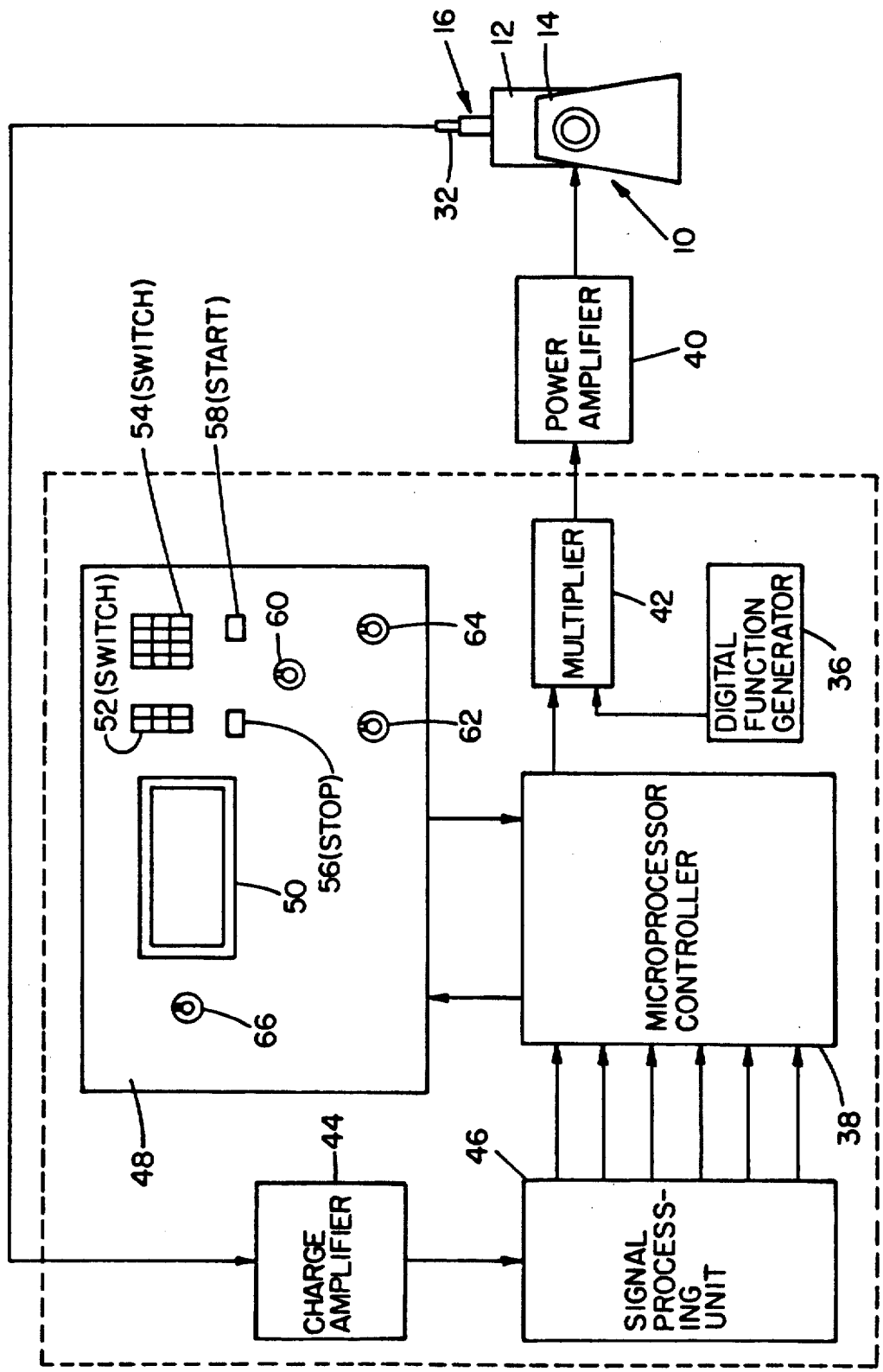
FIG. 1 illustrates an apparatus of the invention diagrammatically.

In the drawing, a B & K-type electromechanical vibrator is indicated with the reference numeral 10. The vibrator has a reciprocating head 12 associated with an electro-magnet exciter body 14. Typically, the head 12 could be a B & K-type 4812 head and the body 14 a B & K-type 4805 body.

Figure 2:
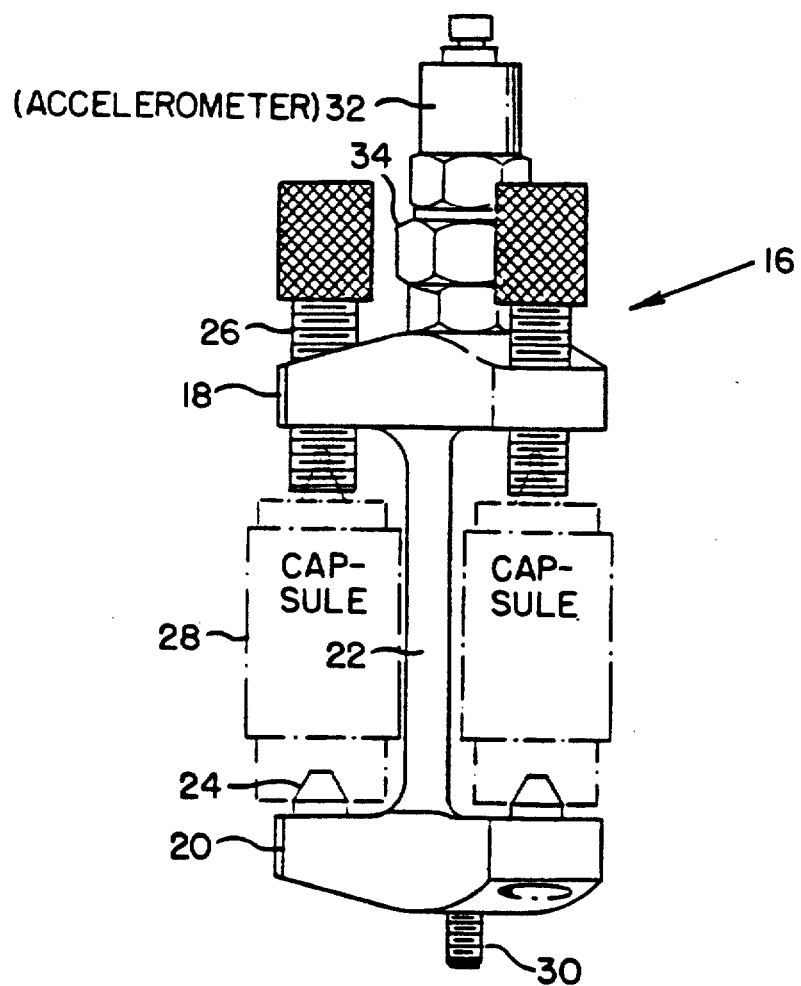
FIG. 2 illustrates the capsule cradle and accelerometer of the apparatus of FIG. 1 in more detail.

Secured to the head 12 of the vibrator 10 is a cradle 16 illustrated in FIG. 2. The cradle 16 has a frame composed of upper and lower flanges 18 and 20 joined by a central section 22. Studs 24 project upwardly from the flange 20 and thumb screws 26 are threaded through the upper flange 18. In use of the apparatus, a number of capsules 28 are clamped between the studs 24 and the thumb screws 26 as illustrated in FIG. 2. The cradle 16 is secured to the head 12 by means of a threaded stud 30. Mounted on top of the cradle 16 is an accelerometer 32 which is separated from the cradle by a mechanical filter 34. Typically, the accelerometer is a B & K 4384 accelerometer and the mechanical filter is a B & K-type UA 0559 filter.

Each capsule 28 is, as illustrated, oriented vertically. Particles, such as diamond grit, which are to be tested for F.I. are placed in each capsule along with a hard, spherical ball of predetermined dimension.

The apparatus of FIG. 1 includes a digital function generator 36 the operation of which is controlled by a microprocessor controller 38 and which is supplied by an oscillator locked to a quartz crystal. The digital function generator 36 delivers a basic drive signal to a power amplifier 40 via a multiplier 42, and the power amplifier provides an exciting signal to the body 14 which drives the head 12 in vertical reciprocation.

The accelerometer 32 associated with the head 12 is sensitive to the vibrations thereof and outputs signal, via a charge amplifier 44, to a signal processing unit 46. The accelerometer 32 can output signals related to the acceleration, velocity or amplitude of the cradle 16 and capsules 28.

The signals delivered by the accelerometer 32 via the charge amplifier 44 are processed by the signal processing unit 46 which computes various characteristic values, such as RMS (root mean square) and peak-to-peak values, of the acceleration, velocity and amplitude parameters. The signal processing unit 46 feeds related signals to the microprocessor controller 38.

The apparatus has a control unit 48 linked to the processor controller 38. The unit 48 includes a control panel for an operator of the apparatus. The panel includes an alpha-numeric display 50 and various manual controls 52 to 66. The control 66 is a display mode switch by means of which data displayed on the display 50 can be changed. A thumb wheel switch 52 is used to set the frequency of vibration of the head 12. A typical frequency in practice would be 40 Hz. A thumbwheel switch 54 is used to set the desired number of cycles through which the head 12 is to vibrate. Stop and start buttons are numbered 56 and 58 respectively. The start button is used to initiate a test cycle and the stop button can be used to stop the machine before the set number of cycles, as dictated by the setting of the thumbwheel switch 54, has been completed. The amplitude of vibration of the head 12 is controlled by operation of a potentiometer control knob 60.

A multi-step rotary switch 62 is provided to enable an operator to select where in a cycle of reciprocation the head 12 should start. Finally, a multi-step rotary switch 64 is provided to enable the operator to select the mode of operation. For instance, this switch may provide the operator with the facility to vary the waveform of the exciting signal fed by the power amplifier 40 to the vibrator 10. Also, the switch 64 affords the operator the facility to choose any one of the three feed-back signals, i.e. acceleration, velocity or amplitude, to be delivered by the accelerometer 32.

The mechanical filter 34 which separates the accelerometer 32 from the cradle 16 is provided to shield the accelerometer from the high frequency impacts of the balls inside the capsules 28 with the ends of the capsules at the end of each upward and downward stroke of the cradle 16.

In operation, the operator selects the desired number of cycles, frequency, amplitude and start position, and also selects a chosen feedback signal for the test under consideration. The apparatus is started and is allowed to run until the required number of cycles has been completed, whereafter the contents of each capsule can be analysed and F.I. values calculated.

One of the advantages of the illustrated apparatus is the fact that operation starts and stops, with controlled acceleration and deceleration, after substantially the exact number of cycles have been executed. This is in contrast to the prior art "FRIATESTER" where mechanical acceleration and deceleration can lead to inaccuracies in the number of operative cycles in a test. Further advantages of the illustrated apparatus when compared to the conventional "FRIATESTER" include the fact that frequency and amplitude of vibration can easily be varied and this makes the apparatus ideal for research purposes. Furthermore, tests conducted by the inventor indicate that the repeatability of F.I. values with the illustrated apparatus is substantially better than with the "FRIATESTER".

I claim:

1. A friability testing apparatus comprising, a capsule for holding a predetermined quantity of particulate material, the friability of which is to be tested, a capsule holder for detachably supporting the capsule, electrically excitable vibrator means for vibrating the capsule holder and capsule, amplifier means for applying an exciting signal to the vibrator means, processingmeans for generating the exciting signal in accordance with one or more predetermined criteria for a predetermined number of vibratory cycles, and a sensor means associated with the vibrator means which is arranged to provide a feedback signal to the processor means to maintain the operation of the vibrator means within predetermined limits, the capsule thereafter being detachable from the capsule holder for subsequent screen analysis of the particulate material therein and computation of a friability index for the particulate material.

2. An apparatus according to claim 1 wherein the predetermined criteria of the exciting signal include one or more of the duration, frequency, amplitude and waveform of the signal.

3. An apparatus according to claim 1 wherein the sensor means is an accelerometer mounted on the capsule holder.

4. An apparatus according to claim 1 and comprising means for selectively varying the frequency of vibration of the capsule holder and capsule, the number of vibration cycles to which the capsule holder and capsule is to be subjected and the amplitude of vibration of the capsule holder and capsule.

5. An apparatus according to claim 4 and comprising a signal processing unit for computing from signals delivered by the sensor means, characteristic values related to the acceleration, velocity or amplitude of vibration of the capsule holder and capsule.

6. An apparatus according to claim 5 wherein the signal processing unit can compute, from signals delivered by the sensor means, RMS and peak-to-peak values for acceleration, velocity or amplitude of vibration of the capsule holder and capsule.

7. An apparatus according to claim 1 wherein the capsule holds a predetermined quantity of diamond particles.

8. A method of testing the friability of diamond particles comprising the steps of, placing a predetermined quantity of diamond particles in a capsule, supporting the capsule releasably on a capsule holder, placing a vibrator and an accelerometer in association with the capsule holder, applying to the vibrator an exciting signal generated by a processor means in accordance with one or more predetermined criteria to cause the capsule holder and capsule to vibrate for a predetermined number of vibratory cycles, directing a feedback signal from the accelerometer to the processor means during operation of the vibrator means to maintain the operation of the vibrator within predetermined limits for a predetermined number of vibratory cycles, thereafter releasing the capsule from the capsule holder, performing a screen analysis of the diamond particles in the capsule, and computing a friability index for the particles.

* * * * *

UNITED STATES PATENT AND TRADEMARK OFFICE
CERTIFICATE OF CORRECTION

PATENT NO. : 5,140,857
DATED : August 25, 1992
INVENTOR(S) : Douglas J. Reid

It is certified that error appears in the above-identified patent and that said Letters Patent is hereby corrected as shown below:

In the Abstract, lines 4 & 5: "microprocssor" should read as --microprocessor--

In the Abstract, line 5: "proivdes" should read as --provides--

In the Abstract, line 8: after "supplies" insert --a feedback--

Signed and Sealed this

Fifth Day of October, 1993

BRUCE LEHMAN

Attest:

Attesting Officer

Commissioner of Patents and Trademarks